US010605817B2

(12) United States Patent
Shiba et al.

(10) Patent No.: US 10,605,817 B2
(45) Date of Patent: *Mar. 31, 2020

(54) AUTOMATIC ANALYZER

(71) Applicant: HITACHI HIGH-TECHNOLOGIES CORPORATION, Tokyo (JP)

(72) Inventors: Masaki Shiba, Hitachinaka (JP); Masaaki Hanawa, Hitachinaka (JP); Masaharu Nishida, Hitachinaka (JP); Hitoshi Otake, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/182,874

(22) Filed: Nov. 7, 2018

(65) Prior Publication Data
US 2019/0072576 A1 Mar. 7, 2019

Related U.S. Application Data

(60) Division of application No. 15/275,679, filed on Sep. 26, 2016, now Pat. No. 10,151,766, which is a
(Continued)

(30) Foreign Application Priority Data

May 14, 2003 (JP) ................. 2003-135260

(51) Int. Cl.
G01N 35/10 (2006.01)
G01N 35/04 (2006.01)
(Continued)

(52) U.S. Cl.
CPC ....... *G01N 35/025* (2013.01); *G01N 35/0092* (2013.01); *G01N 35/00584* (2013.01); *G01N 35/00663* (2013.01); *G01N 35/1002* (2013.01); *G01N 2035/00673* (2013.01); *G01N 2035/0443* (2013.01); *Y10T 436/11* (2015.01); *Y10T 436/114165* (2015.01)

(58) Field of Classification Search
None
See application file for complete search history.

(56) References Cited

U.S. PATENT DOCUMENTS 4,678,752 A 7/1987 Thorne et al.
6,022,746 A 2/2000 Fritchie et al.
(Continued)

FOREIGN PATENT DOCUMENTS

EP 0 510 686 A2 10/1992
EP 0 558 212 A2 9/1993
(Continued)

Primary Examiner — Kathryn Wright
(74) Attorney, Agent, or Firm — Mattingly & Malur, PC

(57) ABSTRACT

A reagent container transfer mechanism transfers a reagent container selected from among reagent containers stored in a second reagent container storage section to a first reagent container storage section. A controller controls the reagent container transfer mechanism to transfer a reagent container from a second reagent container storage section to the first reagent container storage section on the basis of a predetermined priority condition. The predetermined priority condition is one of a reagent provided with an effective calibration curve result, a number of remaining tests, and an expiration date of a reagent.

4 Claims, 4 Drawing Sheets

| PRIORITY | CONDITION |
|---|---|
| 1 | REAGENT INDISPENSABLE TO ANALYSIS START |
| 2 | REAGENT PROVIDED WITH EFFECTIVE CALIBRATION CURVE RESULT |
| 3 | NUMBER OF REMAINING TESTS |
| 4 | EXPIRATION DATE OF REAGENT |

Related U.S. Application Data continuation of application No. 13/423,651, filed on Mar. 19, 2012, now Pat. No. 9,513,302, which is a continuation of application No. 10/844,375, filed on May 13, 2004, now Pat. No. 8,158,058.

(51) Int. Cl.
*G01N 35/02* (2006.01)
*G01N 35/00* (2006.01)

(56) References Cited

U.S. PATENT DOCUMENTS

| | | |
|---|---|---|
| 2004/0057872 A1 | 3/2004 | Shibuya et al. |
| 2005/0013735 A1 | 1/2005 | Gebrian et al. |
| 2005/0014285 A1 | 1/2005 | Miller |

FOREIGN PATENT DOCUMENTS

| | | |
|---|---|---|
| EP | 0 795 754 A2 | 9/1997 |
| EP | 0 845 674 A1 | 6/1998 |
| JP | 2503751 Y2 | 4/1996 |
| JP | 2000310643 A | 11/2000 |
| WO | 94/14073 A1 | 6/1994 |

FIG.2

| PRIORITY | CONDITION |
|---|---|
| 1 | REAGENT INDISPENSABLE TO ANALYSIS START |
| 2 | REAGENT PROVIDED WITH EFFECTIVE CALIBRATION CURVE RESULT |
| 3 | NUMBER OF REMAINING TESTS |
| 4 | EXPIRATION DATE OF REAGENT |

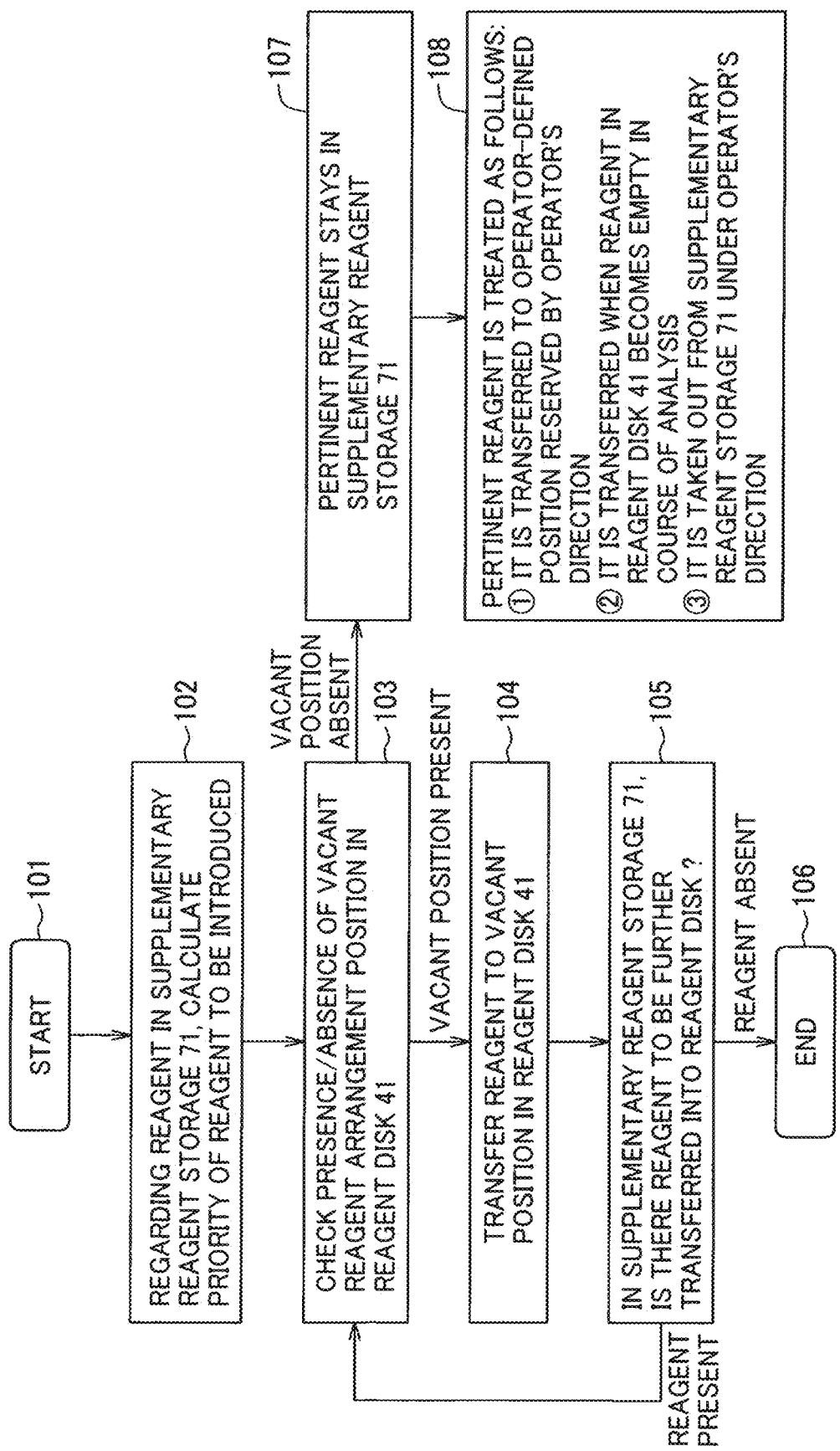

FIG.4

| ITEM | REMAINING AMOUNT | WARNING LEVEL | DIFFERENCE | EXPIRATION DATE |
|------|------------------|---------------|------------|-----------------|
| AST  | 100              | 80            | 20         | //**        |
| ALT  | 600              | 500           | 100        | //**        |
| TP   | 70               | 60            | 10         | //**        |

CALCULATION EXAMPLES OF ESTIMATED REMAINING AMOUNT (AST IS TAKEN AS EXAMPLE)

REMAINING AMOUNT OF AST : 100

REMAINING REAGENT AMOUNT NECESSARY FOR AST ANALYSIS START : 80

DIFFERENCE : 20 TESTS

— 112

109 —
OPERATOR:
PUSH "REAGENT PREPARATION" KEY ON SCREEN

110 —
APPARATUS:
CALCULATE REMAINING REAGENT AMOUNT AND REAGENT AMOUNT NECESSARY FOR ANALYSIS START

111 —
APPARATUS:
TRANSFER REAGENT IN DESCENDING ORDER OF DIFFERENCE BETWEEN REMAINING REAGENT AMOUNT AND REAGENT AMOUNT NECESSARY FOR ANALYSIS START

AUTOMATIC ANALYZER

CROSS REFERENCES

This is a divisional of U.S. Ser. No. 15/275,679, filed Sep. 26, 2016, which is a continuation of U.S. Ser. No. 13/423,651, filed Mar. 19, 2015, now U.S. Pat. No. 9,513,302, which is a continuation of U.S. Ser. No. 10/844,375, filed May 13, 2004, now U.S. Pat. No. 8,158,058, and which claims priority to JP 2003-135260, filed May 14, 2003. The entire disclosures of all of the above-identified applications are hereby incorporated by reference.

BACKGROUND OF THE INVENTION

1. Field of the Invention

The present invention relates to an automatic analyzer that automatically performs a qualitative/quantitative analysis of a biological sample such as blood, urine, or the like, and more particularly to an automatic analyzer capable of mounting many reagents, and having a high throughput.

2. Description of the Related Art

In the field of automatic analysis, a random access type automatic analyzer, which uses a plurality of reaction lines at random, has been developed, and it has brought about a dramatic improvement in processing capability of analysis. With this improvement, the consumption of reagents has speeded up, and opportunities to replace reagents have increased. Automatic analyzers commonly used are of a type in which a plurality of reagent containers are placed on a rotating disk referred to as a reagent disk, and in which, by rotating the reagent disk, an intended reagent is dispensed from an intended reagent container using a reagent dispensing probe. Among these automatic analyzers, Japanese Registered Utility Model No. 2503751 discloses an automatic analyzer in which, with a view to preventing the interruption of an analysis due to the deficiency of a reagent, a plurality of reagent containers each of which contains a kind of reagent that is to be used a lot are set on the reagent disk so that, when one of the reagent containers becomes deficient in the reagent, the reagent can be dispensed from another of the reagent containers. Also, Japanese Unexamined Patent Application Publication No. 2000-310643 discloses an automatic analyzer in which, at the time of replacing a reagent, information on the expiration date of the reagent after the start of its usage is set, and the elapsed time from the start of the usage of the reagent exceeds its expiration date, an alarm is issued.

SUMMARY OF THE INVENTION

In the conventional art, an operator must perform various work, such as the setting of a reagent before an analysis, the checking of a remaining reagent amount, and the registration of the reagent if the reagent is not subjected to barcode management. Even in the event that the operator uses a system such that an apparatus manages a reagent for the operator once he/she has set the reagent into a reagent storage under a reagent barcode management, if depletion of the reagent occurs in course of analysis, it is necessary for the operator to interrupt the analysis, prepare for a new reagent bottle, set it in the reagent storage, and further perform reagent registration work if required. Moreover, in the case of an apparatus having a plurality of reagent storages in order to increase the amount of mountable reagents, or a system of which the capability of analysis processing varies depending on the disposition of reagents in its reagent storage, the operator must unfavorably manage even the disposition of reagents.

Accordingly, it is an object of the present invention to provide an automatic analyzer that reduces the burden imposed on the operator, such as reagent registration and reagent replacement work, that does not cause a deficiency in reagent during analysis, and that minimize the interruption of an analysis.

In order to achieve the above-described object, the present invention provides an automatic analyzer that includes a first reagent container storage section capable of storing a plurality of reagent containers; a reagent dispensing mechanism for dispensing a reagent from a reagent container stored in the first reagent container storage section; a second reagent container storage section capable of storing a plurality of reagent containers; and a reagent container transfer mechanism capable of transferring a reagent container selected from among reagent containers stored in the second reagent container storage section, to the first reagent container storage section. Herein, based on a preset priority, the reagent container transfer mechanism transfers a reagent container from the second reagent container storage section to the first reagent container storage section.

The above-described preset priority in reagent movement may be determined based on the descending order of the difference between the previously stored amount of a reagent necessary for the start of an analysis and the remaining amount of the reagent present in the reagent storage means.

Also, the priority may be registered by the operator. In this case, it is desirable that a display unit capable of displaying a registration screen be provided.

BRIEF DESCRIPTION OF THE DRAWINGS

FIG. 2 is a table showing the priority of reagent introduction according to the embodiment of the present invention;

FIG. 3 is a flowchart of the reagent introduction according to the embodiment of the present invention; and FIG. 4 is a flowchart including a calculation example of remaining reagent amount.

DESCRIPTION OF THE PREFERRED EMBODIMENTS

Figure 1:
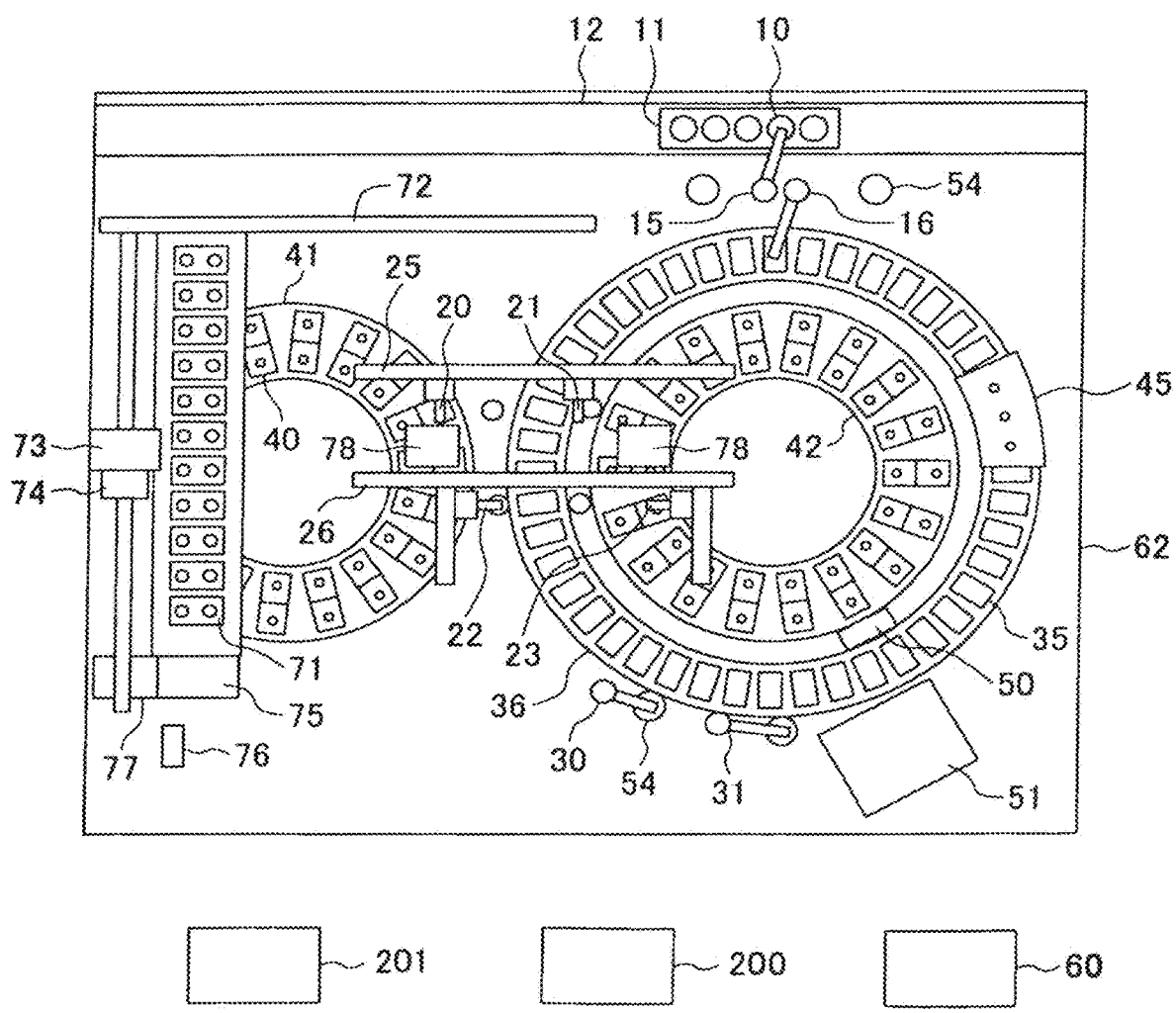
FIG. 1 is a top view of an automatic analyzer according to an embodiment of the present invention.

Hereinafter, the automatic analyzer according to an embodiment of the present invention will be described with reference to the accompanying drawings.

FIG. 1 is a top view of an automatic analyzer according to the embodiment of the present invention. Reaction vessels 35 are arranged along the circumference of a reaction disk 36 on a cabinet 62. A reagent disk 42 is disposed inside the reaction disk 36, while a reagent disk 41 is disposed outside the reaction disk 36. On each of the reagent disks 41 and 42, a plurality of reagent containers 40 can be mounted along the circumference thereof. One reagent container 40 accommodates two reagents. In the vicinity of the reaction disk 36, there is provided a transfer mechanism 12 for moving a rack 11 having sample containers 10 mounted thereon. Rails 25 and 26 are provided above the reagent disks 41 and 42. To the rail 25 there are provided reagent probes 20 and 21 movable in the direction parallel to the rail 25 and in the up-and-down direction. Also, to the rail 26, there are provided reagent probes 22 and 23 movable in three-axis directions with respect the rail 26. The reagent probes 20, 21, 22, and 23 are connected to respective reagent pumps (not shown). Sample probes 15 and 16 that are each rotatable and movable in the vertical direction are disposed between the reaction vessels 35 and the transfer mechanism 12. The sample probes 15 and 16 are connected to respective sample pumps (not shown). Around the reaction disk 36, there are provided stirrers 30 and 31, a light source 50, detection optical unit 51, a vessel cleaning mechanism 45. The vessel cleaning mechanism 45 is connected to a cleaning pump (not shown). A cleaning port 54 is provided within the operating range of each of the sample probes 15 and 16, the reagent probes 20, 21, 22, and 23, and the stirrers 30 and 31. A supplementary reagent storage 71 is disposed on the reagent disk 41. The supplementary reagent storage 71 can mount a plurality of reagent containers. A rail 72 is provided above the supplementary reagent storage 71. To the rail 72, there are provided a reagent holding mechanism 73 and a reagent cap opening mechanism 74 movable in the three-directions with respect to the rail 72. A loading gate 75 for reagent container 40 is provided forward of the supplementary reagent storage 71. In the vicinity of the loading gate 75 for reagent container 40, there is provided a barcode reader 76 for reading a reagent barcode. A waste vent 77 for disposing of reagent caps and used reagent containers 40 is disposed in the vicinity of the supplementary reagent storage 71. The sample pump, reagent pump, and cleaning pump, which are not shown, and the detection optical unit 51, reaction vessel 35, reagent disk 41, reagent probes 20, 21, 22, and 23, sample probes 15 and 16, reagent holding mechanism 73, reagent cap opening mechanism 74, reagent container loading gate 75 are each connected to a controller 60.

An analysis procedure will be described below.

Before entering the analysis, firstly the maintenance of the apparatus is performed. In the maintenance, besides the checking of the detection optical unit 51, the cleaning of the reaction vessels 35, and the cleaning of various probes such as the sample probes 15 and 16, the most important matter is the checking of a reagent in each of the reagent containers 40 mounted on the reagent disks 41 and 42. Regarding information on the reagent containers 40, the mounted positions of reagents in the reagent containers 40, lot numbers expiration dates, remaining reagent amounts, and the like are stored in a control computer. The operator checks conditions of reagent containers in the reagent disks 41 and 42 by CRT 201 or the like. Reagents of which the remaining amount is slight and which might become empty in course of analysis in a day are set in the loading gate 75 for the reagent container 40. The set reagents have the reagent information thereon read by the barcode reader 76, and then transferred to the supplementary reagent storage 71 by the reagent holding mechanism 73. The reagent information read and the information on the mounted positions of the reagents in the supplementary reagent storage 71 is outputted to the control computer 200.

Next, a method for transferring a reagent from the supplementary reagent storage 71 to the reagent disk 41 or 42 is shown in FIGS. 2 and 3. The supplementary reagent storage 71 can mount a plurality of reagents. The present apparatus causes the control computer 200 to previously store the reagent and the reagent amount necessary for an analysis start, which are stored in the apparatus in advance. One possible method for causing the control computer 200 to store them is to input them through the control computer 200. Alternatively, the apparatus may cause an external storage medium to store them. Also, in accordance with its frequency of usage, the present apparatus can also automatically change the reagent and reagent amount that are stored, based on the determination of itself. Using the reagent and reagent amount that are stored in advance, the present apparatus introduces the reagent, for example, in accordance with the priority shown in FIG. 2. FIG. 4 shows an example of calculation of the priority of a reagent indispensable to the start of analysis. As shown in FIG. 4, firstly the operator instructs the apparatus to introduce a reagent (step 109). The apparatus calculates the difference between the reagent amount necessary for the analysis start that has been stored in advance and the amount of the reagent that is present in the reagent disks 41 and 42 (steps 110 and 111). FIG. 3 is a flowchart of the introduction of a reagent. The present apparatus calculates the priority of a reagent to be introduced from the supplementary reagent storage 71 after being subjected to instruction to introduce the reagent (step 102). Thereafter, the apparatus checks whether there is a vacant position in the reagent disks 41 and 42 (step 103). If there is no vacant position, the pertinent reagent stays in the supplementary reagent storage 71 until the condition in step 108 shown in FIG. 3 occurs (step 107). Conversely, if there is a vacant position in the reagent arrangement position in the reagent disk 41 or 42 with respect to the condition in step 103, the present apparatus transfers the pertinent reagent from the supplementary reagent storage 71 to the reagent disk 41 or 42 by the reagent holding mechanism 73 (step 104). After completing the transfer, if there is still a reagent to be further transferred to the reagent disk, in the supplementary reagent storage 71 (step 105), the apparatus repeats the flows in step 103 and the steps thereafter. If there is no reagent in the supplementary reagent storage 71, the processing operation is ended (step 106).

The sample container 10 is charged with an object to be examined, such as blood, and after being mounted onto the rack, is conveyed by the transfer mechanism 12. The sample taken by the sample probe 15 is dispensed in a definite amount into reaction vessels 35 arranged on the reaction disk 36, and then a definite amount of regent is dispensed thereinto from the reagent container 40 disposed on the reagent disk 41 or 42, through the reagent probes 21 or 22. This mixture is stirred by the stirrers 30 and 31, and after undergoing a reaction for a definite time, it is measured by the detection optical unit 51. The measurement results are outputted to the control computer 200. If there is a request to further add measurement items, the above-described sampling operation is repeated. Likewise, regarding all samples on the rack 11, the above-described sampling operation is repeated until the sampling with respect to the set measurement items is completed.

As is evident from the foregoing, since the automatic analyzer according to the present invention includes supplementary reagent storage means and reagent bottle transfer means besides analysis reagent storage mean, it is possible to reduce the burden, such as reagent management, imposed on the operator, minimize the interruption of an analysis due to reagent registration and reagent replacement, mount many reagent thereon, and realize a high throughput.

What is claimed is:

1. An automatic analyzer comprising:
   an optical detector for detecting a reaction in a reaction container containing reagent and sample;
   an identification information reader configured to read identification information applied to a reagent container;

a first reagent container storage section configured to store a plurality of reagent containers;

identification information applied to the reagent container including at least an effective calibration curve result and an expiration date for the corresponding reagent container;

a reagent dispensing mechanism configured to dispense a reagent from a reagent container stored in the first reagent container storage section;

a second reagent container storage section configured to store a plurality of reagent containers;

a reagent container transfer mechanism configured to transfer a reagent container among the reagent containers stored in the second reagent container storage section to the first reagent container storage section;

means for storing information including predetermined priority conditions that indicate a priority from highest to lowest for transferring the reagent container from the second reagent container storage section to the first reagent container storage section; and a controller connected to the reagent container transfer mechanism, the optical detector, the identification information reader, and storage means, configured to:

control the identification information reader to read identification information from respective reagent containers; and control the reagent container transfer mechanism to transfer the reagent container with the highest priority conditions based on the identification information read from the reagent container and the predetermined priority conditions stored in the storage means and transfer to the first reagent container storage section from the second reagent container storage section any reagent container having the highest priority conditions prior to other reagent containers having lower ranked priority conditions, wherein the predetermined priority conditions include including at least a reagent having an effective calibration curve result and an effective expiration date.

2. The automatic analyzer according to claim 1, wherein the predetermined priority conditions include a number of remaining tests of the reagent.

3. The automatic analyzer according to claim 2, wherein the controller is configured to control the reagent control transfer mechanism to transfer the reagent container containing the reagent satisfying the number of remaining tests as the one or more predetermined priority conditions to the first reagent container storage section from the second reagent contained storage section prior to other reagent containers that have been identified by the read identification information, wherein the reagent container containing the reagent satisfying the number of remaining tests has a number of remaining tests that are greater than a number of remaining tests of other reagents contained in other reagent containers that have been identified by the read identification information.

4. The automatic analyzer according to claim 1, wherein the controller is configured to determine the reagent container to be transferred prior to other reagent container on the basis of the effective expiration date of the predetermined priority conditions upon determining no reagent container to be transferred is decided prior to other reagent containers is based on whether the predetermined priority condition of the effective calibration curve result of the contained reagent is satisfied.

\* \* \* \* \*